United States Patent
Clemensen et al.

(10) Patent No.: US 8,240,308 B2
(45) Date of Patent: Aug. 14, 2012

(54) RESPIRATION VALVE

(75) Inventors: Peter Christian Clemensen, Odense (DK); Klas Jorgensen, Odense C (DK)

(73) Assignee: Innovision A/S, Odense S (DK)

( * ) Notice: Subject to any disclaimer, the term of this patent is extended or adjusted under 35 U.S.C. 154(b) by 1197 days.

(21) Appl. No.: 11/665,279

(22) PCT Filed: Oct. 18, 2005

(86) PCT No.: PCT/DK2005/000669
§ 371 (c)(1),
(2), (4) Date: Sep. 24, 2007

(87) PCT Pub. No.: WO2006/042547
PCT Pub. Date: Apr. 27, 2006

(65) Prior Publication Data
US 2009/0266363 A1    Oct. 29, 2009

(30) Foreign Application Priority Data
Oct. 22, 2004 (DK) .................... 2004 01626

(51) Int. Cl.
*A61M 16/00* (2006.01)
*A61M 16/20* (2006.01)
(52) U.S. Cl. ......... 128/205.28; 128/203.11; 128/205.17; 128/206.15; 128/207.12; 128/207.16; 128/205.24
(58) Field of Classification Search ............ 128/203.11, 128/205.28, 206.15, 207.12, 207.16, 205.24
See application file for complete search history.

(56) References Cited

U.S. PATENT DOCUMENTS

| 4,192,301 A | * | 3/1980 | Hardwick | 128/205.17 |
| 4,248,379 A | * | 2/1981 | Hollstein et al. | 239/1 |
| 4,601,465 A | * | 7/1986 | Roy | 482/13 |
| 5,050,593 A | | 9/1991 | Poon | |

(Continued)

FOREIGN PATENT DOCUMENTS

CA    2 299 913    9/2000
(Continued)

OTHER PUBLICATIONS

Machine Translation of Hayashi et al (JP 2004-293782 A), Oct. 21, 2004, provided by the Japanese Patent Office, pp. 1-23.*

*Primary Examiner* — Clinton T Ostrup
(74) *Attorney, Agent, or Firm* — Day Pitney LLP; Brian R. Pollack

(57) ABSTRACT

The present invention relates to a respiration valve (401) for performing respiration tests on e.g. humans, consisting of at least three ports, a first mouth port (402) and two breathing ports (403, 404). The breathing ports (403, 404) comprise pneumatic pinch valves consisting of a channel (101) with a flexible wall (201) to be used for the flow of material and molded as an integrated part of a surrounding chamber (102). The flexible wall (201) comprises two opposing angularly interconnected wall segments (202) which are angularly connected at interconnection points (203) and which flexible wall (201) is pinched by a pressure from fluid, such as air, introduced into the chamber (102). The cross sectional shape corresponds in one embodiment approximately to a elongated hexagon. The construction of the respiration valve (401) comprising these pneumatic pinch is valves enables a very small, light, hygienic, and safe yet inexpensive construction with a long life expectancy. The respiration valve (401) is preferably completely or partially made of silicone rubber.

9 Claims, 4 Drawing Sheets

U.S. PATENT DOCUMENTS

| | | | |
|---|---|---|---|
| 5,119,825 A * | 6/1992 | Huhn | 600/529 |
| 6,102,361 A | 8/2000 | Riikonen | |
| 6,604,523 B2 * | 8/2003 | Lurie et al. | 128/205.24 |
| 2002/0117173 A1 | 8/2002 | Lynn et al. | |
| 2004/0075069 A1 * | 4/2004 | Bartoli et al. | 251/5 |
| 2005/0158187 A1 * | 7/2005 | Fulkerson et al. | 417/390 |

FOREIGN PATENT DOCUMENTS

| | | |
|---|---|---|
| EP | 0 154 104 | 9/1985 |
| EP | 0 700 687 | 3/1996 |
| EP | 0 990 448 | 4/2000 |
| FR | 2 693 784 | 1/1994 |
| JP | 2004293782 | 10/2004 |
| JP | 2004293782 A * | 10/2004 |
| SU | 397725 | 9/1973 |
| WO | WO 96/17173 | 6/1996 |
| WO | WO 00/17549 | 3/2000 |

* cited by examiner

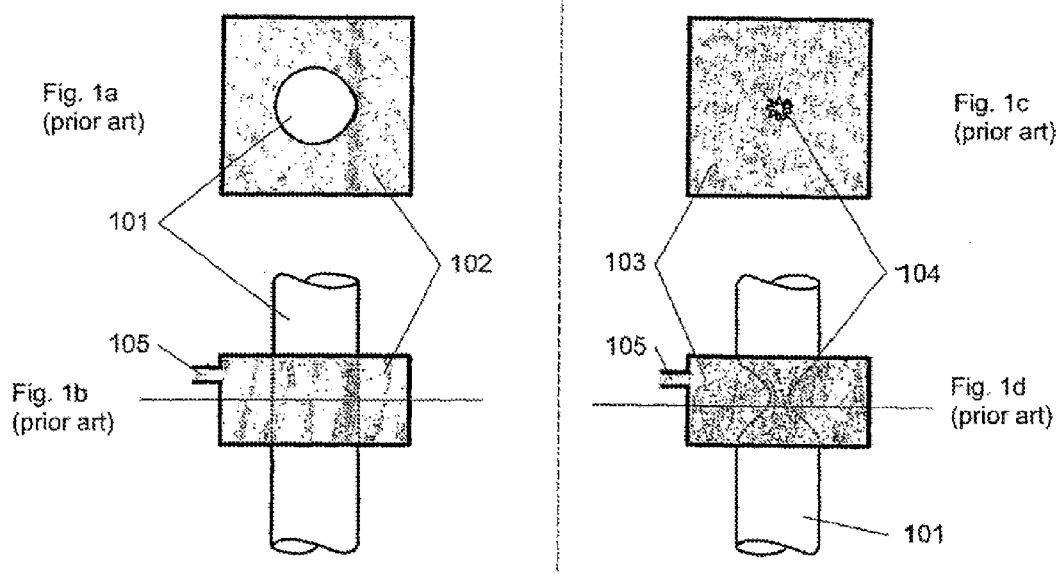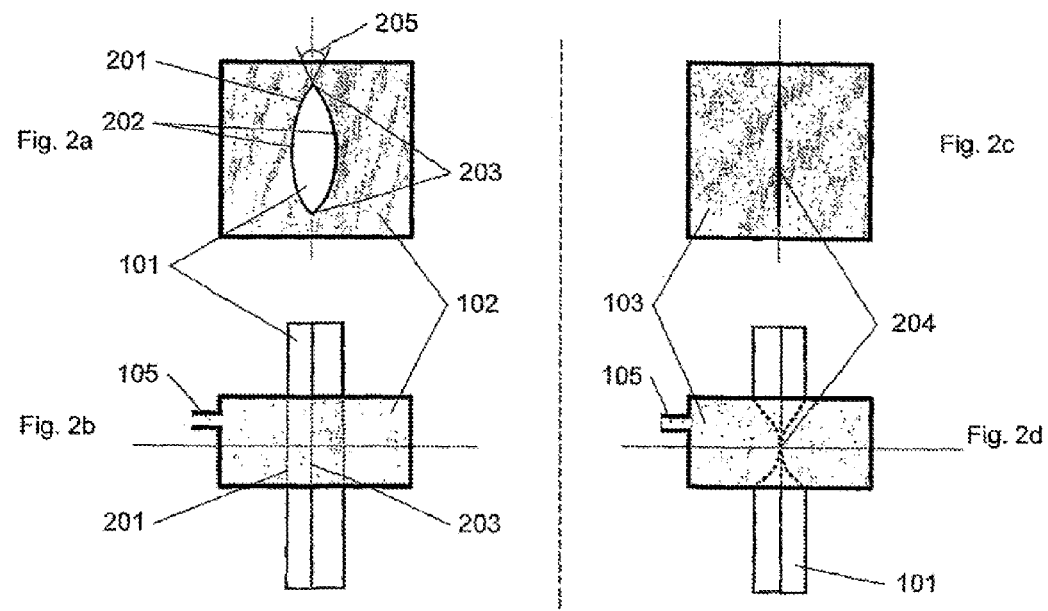

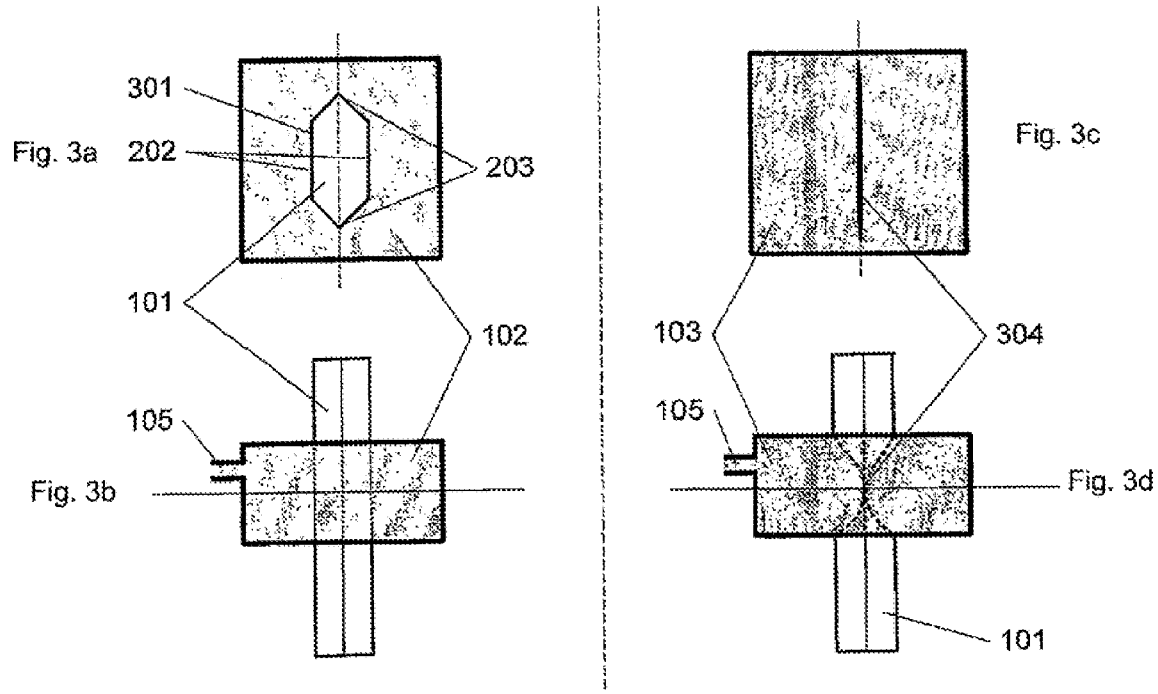

RESPIRATION VALVE

The present invention relates to a respiration valve for performing respiration tests on e.g. humans, where the respiration valve comprises pinch valves.

BACKGROUND OF THE INVENTION

One way of measuring and examining the well-functioning and performance of a patient's heart is by determining the cardiac output. A well-established method or principle to measure the cardiac output is by inert gas rebreathing, which is a non-invasive measurement method. This principle utilizes a closed rebreathing system where a small amount of a blood soluble, physiologically inert gas is inhaled from a rebreathing bag. Among other things, a concentration curve of the inert gas can be extracted from the measurements during rebreathing and the wash-out rate, which is proportional to the cardiac output, can be calculated. During the measuring, the patient is breathing through a respiration valve which allows switching from breathing air to rebreathing the inert gas mixture from the bag and switching back again. A similar respiration valve is used in other cardiopulmonary tests such as in determination of the lung volume or the diffusing capacity of the lung, where the ability of the lung membrane to transport gases is determined. In general it can be used in rebreathing tests and in single breath or multiple breath wash out tests.

Different types of both manually, mechanically, and pneumatically operated valves have been used to date for cardiopulmonary testing. One type of mechanically operated valve used in respiration valves is a manually operated sliding or rotating type of valve where the flow is shut off by a moving inner part. Also metal flap valves opened and closed manually or by pneumatics have been used. Yet another type of valve that has been used is the inflatable balloon, in which a small balloon-like element is placed centrally in the flow channel and blown up to stop the flow. However, all of these types of valves in a respiration valve yield several problems and disadvantages. Firstly, any parts intruding into the flow are to be avoided as they increase the flow resistance and thereby affect the patient's breathing. Secondly, any metal parts make the valve far more clumsy, heavy, and take up a considerable amount of space. All of these points are very important in the design of a respiration valve, which is to be connected to a patient's mouth for a certain period of time and therefore must be small and light. Also if possible, metal parts are to be avoided in an item as a respiration valve which is in close contact with different humans (or animals), their moisture and saliva, both for sanitation reasons and for mechanical reasons as the metal deals poorly with such environmental conditions. Furthermore, a mechanically operated valve is sensitive to wear and fatigue during many opening and closing operations.

A pneumatic pinch valve can in its simplest form consist of a cylindrical flexible tube sealed in each end to a substantially rigid co-axial valve body carrying the tube, where the flexible tube, when subjected to a fluidic force from the surrounding fluid (e.g. air), is pinched together and closes. However, such a cylinder will inevitably form foldings and wrinkle when pressed together. A valve like this will not be able to close tightly unless the pressure in the surrounding fluid is relatively high, and furthermore, as the shape and the area of the opening are uncontrollable, the valve will be unsuitable for regulation purposes.

The pneumatic pinch valve described in CA 2299913 is a circular flexible tube in a rigid valve body where the flexible inner tube collapses along a lateral constriction seam hereby avoiding the undesired wrinkles mentioned above. In order to ensure that the tube will actually collapse in the desired fashion, a repetitive series of conditioning pre-manipulations is performed on the tube. This means that the cylinder is subjected to a substantial and somewhat permanent deformation giving the cylinder wall a crease at the desired positions. An alternative mentioned in the patent is to reduce the wall thickness at the desired bending points or lines. This valve construction contains the advantage of being very simple and with the possibility of being very compact and small. Nevertheless, some big problems still remain. First, although the wrinkling is avoided, a valve as described above still cannot close completely in the corners at the ends of the constriction seam due to the shape of the cylinder unless the pressure in the surrounding fluid is relatively high. Second, the steps taken to ensure that the tube is pinched together along a linear seam instead of the uncontrollable folding have inevitably damaged the tube to some extent, thereby reducing the lifetime of the valve and also reducing the resistance to wear and fatigue considerably.

Another pneumatic pinch valve is described in the patent WO 0017549, where a flexible diaphragm in a tube is compressed by air pressure. In the open condition the diaphragm is circular and in the closed condition the membrane folds and is pinched together around a set of guiding vanes, one in each side inside the membrane. This valve has solved the aforementioned problem with incomplete and uncontrollable closing and can be advantageous in large scale structures such as in ventilation ducting and in conveyors for powder transport. The guiding vanes inside the membrane, however, lead to more parts in the valve which complicates the structure and the manufacturing hereof, also because the guiding vanes are of a rather complicated geometrical shape. This valve is therefore more expensive to produce and cannot be made as compact or small, the larger dimensions again also leading to the need for a higher air pressure to close the valve. Furthermore, the guiding vanes inside the tube are undesirable in many applications as they increase the flow resistance considerably. Also the pinch shape of this valve makes the membrane walls pass a snap-through under increasing pressure from the open to the closed position. During such a snap-through the open flow area changes very fast and suddenly leading to difficulties in adjusting and regulating the flow. The valve is thus not so adequate for regulation purposes.

U.S. Pat. No. 5,119,825 describes a single-use, disposable patient valve for the use in cardiopulmonary tests. Here, the patient breathes through a mouthpiece on the other side of which is placed a first valve. If activated, the patient is forced to hold his breath. The mouthpiece is then connected to three channels, one of which is connected to a gas supply regulated by a demand valve. The second channel leads to a collection tube and the third leads to atmospheric air, which passage can also be opened or closed by a valve. Both valves work by a mechanically operated piston pinching off the circular flexible channels. Although avoiding any moving parts protruding into the flow, the proposed respiration valve possess a number of disadvantages. The construction of the valves themselves yields a heavy and clumsy design leading to a quite heavy and big apparatus which is inappropriate in the testing situation of patient, both for a patient at rest, but even more so for measurements made on a patient during different physical tests. A further disadvantage is the mechanical moving parts which although they are not in direct contact with the breathing of the patient remain a hygienic problem. Also, the design of the respiration valve with the placing of the pinching valves is disadvantageous as the dead space between the two valves is considerable rendering the measurements correspondingly inaccurate.

OBJECT AND SUMMARY OF THE INVENTION

It is therefore an object of the present invention to obtain a user friendly respiration valve for respiration tests where the air and gas flows can be regulated in a very simple and fast way without the above mentioned problems. A further object is to obtain a very compact, light, and hygienic respiration valve.

The invention relates to a respiration valve to be used for performing respiration tests on e.g. humans, wherein the respiration valve comprises at least three ports, a first mouth port and two or more breathing ports and, wherein these breathing ports comprise valves to control flow through the breathing ports and wherein at least one of these valves is a pneumatic pinch valve. A respiration valve according to this invention can be made without any mechanically moving parts, very small, compact, and light which is very advantageous for this type of apparatus, that is to be connected to a patient's mouth for a certain period of time. The use of one or more pneumatic pinch valves makes the handling and operation of the respiration valve very simple, yet highly reliable. By using two pinch valves the switching of the valves to allow inhalation of the gas mixture can be performed fully automatically in a very fast and precise manner which is of the utmost importance for the quality of the measurements made with the patient breathing through the respiration valve. Because of the compactness of the invention, the amount of pneumatic gas needed is kept to a minimum. Also the dead space between the two breathing ports is very small, which further increases the accuracy of the measurements. As the pinching valves are without any parts protruding into the channels and with smooth inner surfaces, the flow resistance can be kept very low through the valves. In fact, the dimensions of the channels in the valves can be chosen such that the flow in the open position of the valves is basically unaffected by the presence of the valves. This is of high importance in a respiration valve, where the breathing of the patient is to be hindered as little as possible by the apparatus. The geometry of the pinch valves further facilitates cleaning and rinsing of the respiration valve. Finally, a respiration valve as described above can be produced with low manufacturing costs in a safe and standardized process.

In another embodiment of the invention each of the breathing ports in the respiration valve according to the above comprises one valve, whereby it is possible to effectively regulate and control the flow from each intake independently of the others. Furthermore, in this way the dead space between the valves can be minimized as the breathing ports can be placed in close connection to each other.

In a further embodiment of the invention one of the breathing ports is connected to the atmospheric air and another of said breathing ports is connected to a rebreathing bag.

The invention furthermore concerns a respiration valve according to the above, wherein the pneumatic pinch valve comprises a channel with a flexible wall in which channel the material flows. The channel is molded as an integrated part of a surrounding chamber and the valve functionality is obtained by pinching the flexible wall based on pressure from fluid, such as air, introduced into the chamber. The flexible wall of the channel is characterized by comprising two opposing angularly interconnected wall segments being angularly connected at interconnection points, where these two wall segments are pinched towards each other based on pressure from the fluid. The pneumatic pinch valve according to the invention presents a geometrically very simple design made out of only very few parts and no mechanically moving parts. It can thus be made very small and compact and at the same time very robust and inexpensive. Because of the small size, it can also be made very light. Furthermore, the air or fluid pressure needed to operate the valve is very low because of the flexibility and shape of the channel and because the volume of the pressure chamber can be made small. Because the wall segments are angularly connected at interconnection points, the shape of the flexible channel is well defined and controllable not only in the fully opened and closed positions but also at all positions in-between. This thus makes the pinch valve according to the invention extremely suitable also for the continuous regulation of a flow and not only for shutting it off or opening it. Also, the valve design contains the important quality of closing the channel completely, even if dust or dirt particles are present in the material flow. Compared to prior art, the present valve is further advantageous by not having weak and seriously stressed regions because the closing shape is already built into the design by the angular connection of the wall segments. In other words, the pinch valve is not as prone to fatigue and wear and has a long life expectancy. Yet a further advantage of the present invention is the absence of any parts protruding into the flow channel which together with the smooth inner surfaces in the channel keep the flow resistance in the channel low. By choosing the distance between the interconnection points in the valve in accordance with the geometry and size of the channel before and after the valve, one can even obtain that the flow resistance is not affected by the presence of the valve in its open configuration. The above mentioned properties also facilitate the cleaning and rinsing of the channel.

In another embodiment of the invention the wall segments of the pinch valve in a respiration valve are angularly connected with an acute angle between the wall segments.

In a further embodiment of the invention the channel in a pinch valve in a respiration valve as described above has a cross sectional elongated shape, whereby the distance between the interconnection points is larger than the distance between the two opposing wall segments. This shape is advantageous in that the pressure needed to pinch the wall segments together to a closed position is lower as the wall segments are close to each other.

Another embodiment of the invention concerns a respiration valve comprising a pinch valve according to the above wherein the cross sectional elongated shape approximately corresponds to a hexagon.

In a preferred embodiment the flexible wall of the pinch valve is made from silicone rubber (elastomer). This specific choice of material is advantageous as it is a light material which has excellent elastic properties, high tensile strength and does not exhibit hysteresis, meaning that it has good closing and reopening properties. It also has a high resistance to chemicals and is thermally stable and unaffected by environmental extremes. It also has good medical and sanitary properties including physiological inertness and high tolerance to humidity. Furthermore, the pinch valve can be moulded in only one single or a very few parts using the silicone.

Another embodiment of the invention concerns a respiration valve comprising a pinch valve according to the above wherein the pneumatic pinch valve is made as a hybrid comprising a flexible wall made of silicone rubber and a chamber made of a plastic. Hereby is obtained a reduction of the wall thicknesses in areas and thus a corresponding reduction of the overall weight of the respiration valve.

In another embodiment of the invention the respiration valve according to the above is made from silicone rubber.

The advantages of this material being the same as described for the pneumatic pinch valve.

BRIEF DESCRIPTION OF THE DRAWINGS

In the following preferred embodiments of the invention will be described referring to the figures, where FIGS. 1a-1d illustrate schematically the functioning of a pinch valve as known in the art, FIGS. 2a-2d illustrate a pinch valve as used in a respiration valve according to the invention, FIGS. 3a-3d illustrate another embodiment of a pinch valve used in a respiration valve according to the invention.

DESCRIPTION OF PREFERRED EMBODIMENTS

Figure 4A:
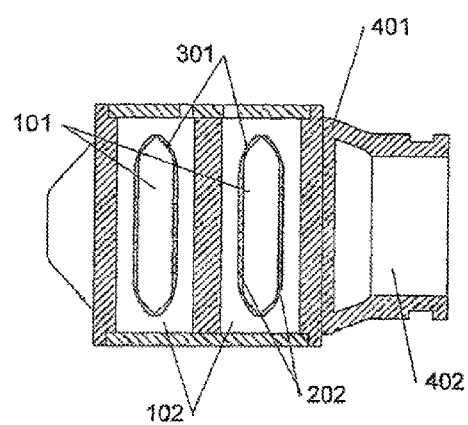
FIGS. 4a-4d illustrate a respiration valve according to the invention in the configurations of both pinch valves open, and one valve open and the other closed.

FIGS. 1a-1d illustrate the principle of a pneumatic pinch valve as known in the art. FIGS. 1a-1b illustrate top and side views of the open configuration of the valve, while FIGS. 1c-1d illustrate top and side view of the closed configuration. A cylindrical channel or tube 101 is surrounded by a chamber 102 with an injection port 105, and in close connection to the channel 101. When the chamber 102 is filled with air or some fluid under pressure 103 the cylindrical channel 101 will be pinched as shown schematically in FIGS. 1c-1d and the valve is closed. However, if the channel 101 is a conventional more or less circular tube, the valve will have difficulties in closing completely as the tube will wrinkle in compression 104 in some undefined shape not known a priori. Furthermore, this wrinkling 104 leads to severe wear and fatigue of the channel material even after a relatively few closing and opening operations of the valve.

FIGS. 2a-2d illustrate a pinch valve as used in a respiration valve according to the invention. As in the prior figures, FIGS. 2a-2b illustrate top and side view of the open configuration of the valve, while FIGS. 2c-2d illustrate a top and side view of the closed configuration. The channel 101 with the flow regulated by the valve is surrounded by a chamber 102 with an injection port 105. The channel 101 is designed as a tube with a flexible wall 201, comprising two opposing wall segments 202 connected angularly at interconnection points 203. The two wall segments 202 are in this embodiment of the invention connected at an acute angle 205. The cross sectional shape is furthermore symmetric and elongated such that the largest distance between the two opposing wall segments 202 is smaller than the distance between the interconnection points 203. Only the design of the part of the channel inside the chamber 102 is of importance. Outside the chamber 102 the channel 101 could have any arbitrary shape or cross section. The two-sided channel is designed such, that the two wall segments 202 are pinched together and close the channel completely 204 when pressure is applied to the chamber 103. This is illustrated in FIGS. 2c-2d.

The pressure needed to close the channel is minimal because of the cross sectional shape and the flexibility of the wall segments 202. Also, due to the well defined shape of the cross section of the channel at increasing pressure in the chamber 102, the flow through the channel 101 can be controlled precisely by the pressure and regulated precisely from fully open to fully closed and all positions in-between. Furthermore, the shape leads to only minimal stresses in the flexible channel wall 201 even in the fully closed and deformed position 204 as the problematic stresses occurring at the bending locations of a conventional tube are avoided by the angular interconnection 203 of the wall segments 202. A further advantage of the valve is the absence of any parts protruding into the channel which would inevitably increase the flow resistance. It is also advantageous that the valve is without any mechanically moving parts. Furthermore, it is possible to manufacture the valve as a one-piece in silicone, a thermoplastic elastomer or the like. The pinch valve can also be manufactured as a hybrid of different materials where for instance the wall segments of the channel are made in a flexible material like silicone and the chamber is made in a more rigid and inexpensive material like for instance a plastic. Hereby, the wall thicknesses of the chamber can be made smaller and the weight minimized.

Another embodiment of a valve which advantageously can be used in a respiration valve according to the invention is shown in FIGS. 3a-3d. Here, the cross sectional shape of the channel 101 is formed in large as an elongated hexagon 301. This design also allows the channel to close completely 304 when pressure is applied to the chamber 103. The channel could also be shaped as an elongated hexagon with straight walls if more advantageous for example for production reasons. The part of the channel passing through the chamber 102 may also be of the shape as a rhomb or any convex multisided polygon as long as the shape is such, that the wall segments 202 will be pinched together in a controlled and well defined manner when the pressure is applied exterior to the channel. This controlled folding can be achieved if two interconnection points 203 on the periphery of the cross section are situated so, that the distance between them following the circumference of the channel the one way around or the other is just about the same.

Figure 4B:
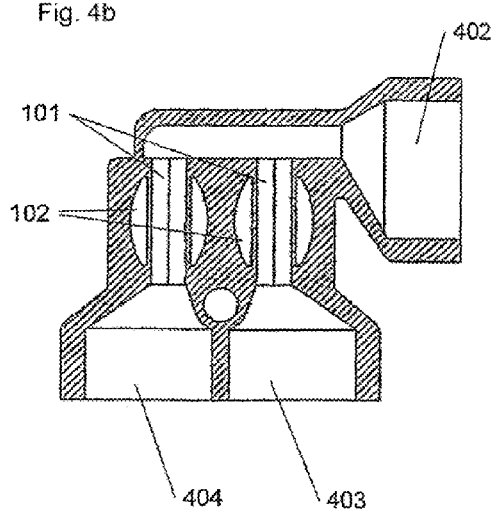
Figure 4C:
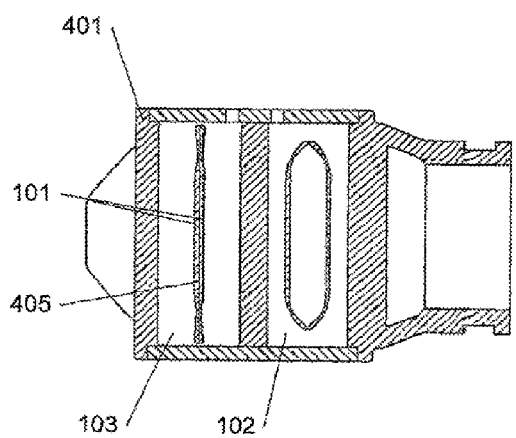
Figure 4D:
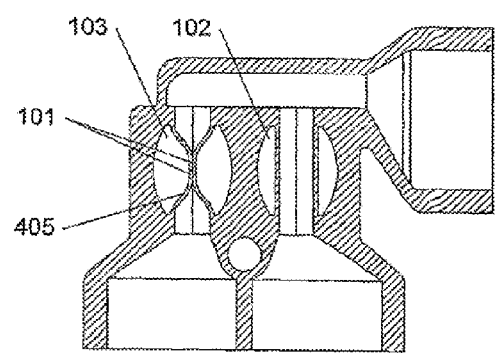

FIGS. 4a-4d illustrate a respiration valve 401 for performing respiration tests on humans or animals. FIGS. 4a-4b illustrate the respiration valve 401 in a top and side view with both pinching valves in open positions. FIGS. 4c-4d illustrate the same respiration valve 401 from the top and the side, but with one of the pinching valves being closed. The respiration valve 401 contains three ports—one mouth port 402, and two breathing ports 403 and 404. The port 402 forms a mouthpiece or mouthpiece connection into which the patient inhales and exhales. The air that the patient breathes comes from either of the two ports 403 and 404, where one of the ports 403 is normally connected to the atmospheric air, while the other port 404 is connected to a rebreathing bag (not shown) filled with a blood soluble, physiologically inert gas mixture. The two breathing ports 403 and 404 can also be used in the opposite configuration. According to the invention the two breathing ports 403 and 404 comprise a pneumatic pinch valve each. These pneumatic pinching valves can preferably be of the types and principle illustrated in the previous FIGS. 2-3. As can be seen in the upper drawings in the figure, the channels 101 leading from the two ports 403 and 404 to the mouthpiece 402 are in this embodiment of the invention made of flexible wall segments 202 shaped in cross section as elongated hexagons as described in FIGS. 3a-3d. Both pinch valves are fully opened in FIGS. 4a-4b. Each of these valves is fully or partially closed independently by letting compressed air into the small closed chambers 102 surrounding each channel 101. By default, the pinch valve above the breathing port 403 is open whereas the pinch valve above the breathing port 404 is closed (pressurised) by default. To initiate a rebreathing manoeuvre the two pinch valves are switched e.g. with a short delay between the operation of the individual pinch valves. The air pressure can for instance be controlled by a computer controlled solenoid valve in connection with a source of compressed gas (not shown), whereby the operation compared to the operation of a manually controlled valve is eased and simplified dramatically. In FIGS. 4c-4d the pinch valve 405 is in its fully closed position, where the two opposing wall segments 202 are pinched together. As these chambers surrounding the channels are small in dimensions, the switching (closing and opening) can be performed very fast and with only the need for a low air pressure. A big advantage of the invention is the compactness of the pinch valves which together with the overall constructional design of the respiration valve makes the whole respiration valve compact and small and therefore lighter. Furthermore, the compactness of the valves and the design and placing of the two breathing ports means that the dead space between the ports 403 and 404 is kept at a minimum which is of high importance to the quality of the measurements. The exact placing of the three ports in relation to each other in the respiration valve is not necessarily of special importance as long as both the overall size and the dead space are kept minimal. In other embodiments of the invention the ports are placed differently such as for instance with the port 403 lying opposite the port 404 or opposite port 402 forming or connecting to the mouthpiece. The respiration valve can in this embodiment shown in the figures be produced as one single unit out of for instance silicone or a thermoplastic elastomer with an appropriate flexibility. A possibility according to the invention is to further reduce the amount of the relatively expensive silicone rubber material used in the respiration valve and thereby also the weight by reducing the wall thicknesses of the pinch valve chambers. The stiffness of the chamber walls needed to keep down the pneumatic pressure closing the valves could then be obtained by embedding the respiration valve in a rigid housing made of a more inexpensive yet more rigid and lighter material like for instance a plastic. In yet another embodiment the pinch valve is manufactured as a hybrid of different materials, where for instance the wall segments of the channel are made in a flexible material like silicone and the chamber is made in a more rigid and inexpensive material like for instance a plastic. Hereby, the wall thicknesses of the chamber can be made smaller and the weight minimized. A further advantage by the respiration valve shown in the figures is that the distances between the interconnection points in the pinch valves compared to the diameters of the ports are chosen such that the flow resistance everywhere in the respiration valve is basically the same. Hereby, the breathing by the patient is obstructed as little as possible by the respiration valve, which is important in order not to affect the patient's breathing.

Figure 5A:
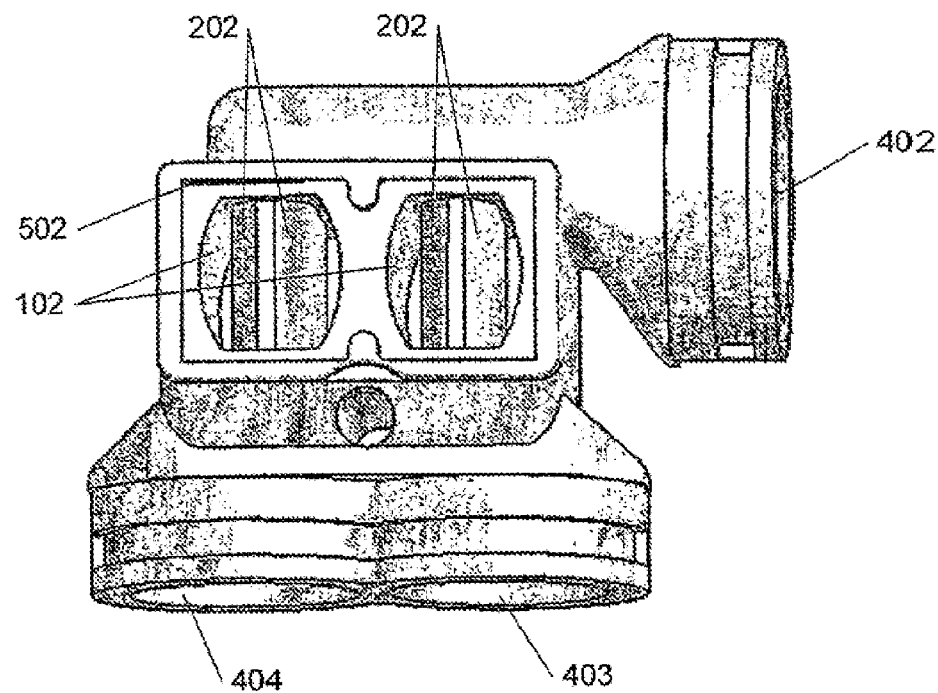
FIGS. 5a-5b illustrate the exterior design of a respiration valve according to the invention.
Figure 5B:
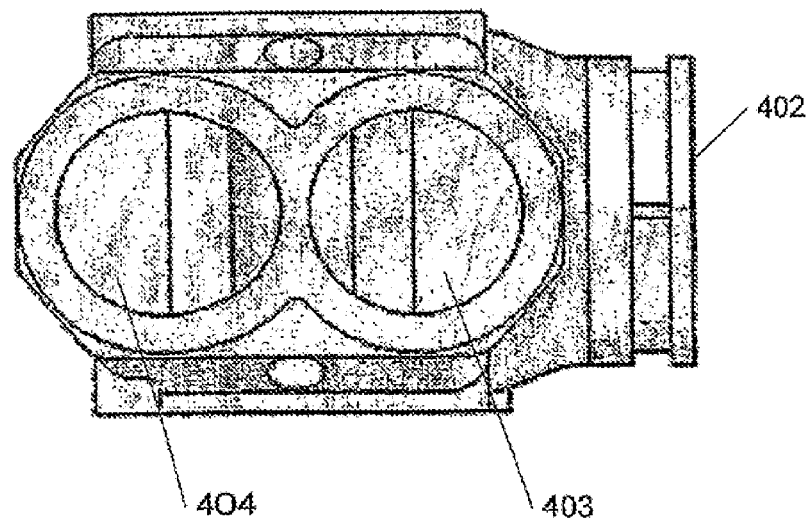

FIGS. 5a-5b illustrate a design of the respiration valve 401 as it can be produced in one single piece. FIG. 5a illustrates the valve from the side and slightly below. Here, the channel wall segments 202 in the two, in this case, open pneumatic pinch valves can be seen. The chambers 102 around the channels are open due to manufacturing reasons, but are to be closed and separated by a cover or a cork on each side of the respiration valve of a shape following the contour 502. The cover can for instance be welded or glued onto the main piece. The air supplies controlling the air pressure in each chamber 102 independently are in this design led through small openings in the cover. FIG. 5b illustrates the respiration valve from the bottom with the two breathing ports 403 and 404.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word 'comprising' does not exclude the presence of other elements or steps than those listed in a claim. The invention can be implemented by means of hardware comprising several distinct elements, and by means of a suitably programmed computer. In a device claim enumerating several means, several of these means can be embodied by one and the same item of hardware. The mere fact that certain measures are recited in mutually different dependent claims does not indicate that a combination of these measures cannot be used to advantage.

The invention claimed is:

1. A respiration valve 401 to be used for performing respiration tests on humans,
    wherein said respiration valve comprises at least three ports, a first mouth port 402 and two or more breathing ports 403 and 404,
    wherein said breathing ports comprise valves to control flow through said breathing ports and wherein at least one of said valves is a pneumatic pinch valve comprising a channel 101 with a flexible wall 201 to be used for said flow,
    said channel 101 being molded as an integrated part of a surrounding chamber 102, and
    where said flexible wall 201 of the channel 101 comprises two opposing angularly interconnected wall segments 202 being angularly connected at interconnection points 203 and wherein said two wall segments are pinched towards each other and close the channel completely based on pressure 103 from fluid introduced into said chamber, said pressure acting approximately equally on said two opposing angularly interconnected wall segments 202.

2. A respiration valve 401 according to claim 1, wherein each of said breathing ports comprises one valve.

3. A respiration valve 401 according to claim 1, wherein one of said breathing ports is connected to the atmospheric air and another of said breathing ports is connected to a rebreathing bag.

4. A respiration valve 401 according to claim 1, wherein said segments 202 in said pneumatic pinch valve are angularly connected with an acute angle 205 between said wall segments.

5. A respiration valve 401 according to claim 1, wherein said channel in said pneumatic pinch valve has a cross sectional elongated shape, whereby the distance between said interconnection points 203 are larger than the distance between said two opposing wall segments 202.

6. A respiration valve 401 according to claim 5, wherein said cross sectional elongated shape in said pneumatic pinch valve approximately corresponds to a hexagon 301, a rhomb, or to a convex multisided polygon.

7. A respiration valve 401 according to claim 1, wherein at least said flexible wall in said pneumatic pinch valve is made from silicone rubber.

8. A respiration valve 401 according to claim 1, wherein said pneumatic pinch valve is made as a hybrid comprising a flexible wall made of silicone rubber and a chamber made of a plastic.

9. A respiration valve 401 according to claim 1, wherein said respiration valve is made from silicone rubber.

* * * * *